United States Patent [19]

Hankinson

[11] 3,963,023
[45] June 15, 1976

[54] EXTRACORPOREAL BLOOD CIRCULATION SYSTEM AND PUMP

[75] Inventor: George R. Hankinson, Littleton, Colo.

[73] Assignee: Cobe Laboratories, Inc., Lakewood, Colo.

[22] Filed: Nov. 4, 1974

[21] Appl. No.: 520,198

[52] U.S. Cl. ............................ 128/214 F; 417/477
[51] Int. Cl.² .................. A01M 1/02; F04B 43/08; F04B 43/12; F04B 45/06
[58] Field of Search ........... 417/477, 475, 476, 474; 128/214 R, 214 F

[56] References Cited
UNITED STATES PATENTS

| | | | |
|---|---|---|---|
| 3,192,863 | 7/1965 | Vadot | 417/477 |
| 3,658,445 | 4/1972 | Pulman et al. | 412/474 |
| 3,756,752 | 9/1973 | Stenner | 417/477 |
| 3,822,948 | 7/1974 | Handl | 417/477 |
| 3,841,799 | 10/1974 | Spinosa | 417/477 |

*Primary Examiner*—Carlton R. Croyle
*Assistant Examiner*—Richard E. Gluck
*Attorney, Agent, or Firm*—Reising, Ethington, Barnard, Perry & Brooks

[57] ABSTRACT

In accordance with the invention there is provided an extracorporeal blood circulation system for circulating a patient's blood from and then back to the patient through tubing at least a portion of which is flexible, and a roller-type blood pump for coaction with the flexible tubing to cause movement of the blood through the system, the pump having means for conveniently and automatically positioning the flexible tubing in its operative position within the pump.

14 Claims, 6 Drawing Figures

EXTRACORPOREAL BLOOD CIRCULATION SYSTEM AND PUMP

The subject matter of the present invention is an extracorporeal blood circulation system and pump for circulating a patient's blood from the patient, through the system, and then back to the patient.

Extracorporeal blood circulation systems are used for circulating a medical patient's blood through, for example, an artificial kidney located external of the patient. Such a system comprises a tube for withdrawing blood from the patient to the artificial kidney, the artificial kidney itself, and a tube for returning the blood from the artificial kidney to the patient. To augment the heart of the patient in causing circulation of the blood through the system, the system itself includes a pump — preferably a roller-type pump. In a roller-type pump a flexible portion of the blood-conducting tubing of the system rests against backing, generally of arcuate shape having a uniform radius of curvature, and spaced rollers are rolled along flexible tubing in resiliently biased contact therewith such that as each of the rollers moves along the tubing it occludes or squeezes the tubing closed and thereby pumps the blood through the tubing in the direction of movement of the rollers. A roller-type pump is much preferred for extracorporeal blood circulation systems because such a pump provides a sealed system, with the tubing of the system itself functioning as a part of the pump, because it provides ease in assuring sterility and, further, because such a pump causes minimum turbulence to the blood thereby minimizing the possibility of turbulence-caused hemolysis of blood within the system.

However, one of the difficulties with such pumps as they have heretofore been used in extracorporeal blood circulation systems is the skill required and inconvenience involved in assuring proper placement of the flexible tubing between the backing and the resiliently biased rollers. Also, there is some hazard of injury to the medical attendant's hands in performing the task. Even for a skilled medical attendant is has heretofore required considerable time and care to assure proper insertion of the flexible tube against the backing and underneath the rollers. For systems designed for operation in the home by the patient, without benefit of a medical attendant, all the more so has there been need for a roller type blood pump which allows for safe, simple, automatic placement of the flexible tube between the backing and the rollers.

It is the principal object of the invention to fulfill the aforesaid need. That is, it is the principal object of the present invention to provide an extracorporeal blood circulation system and pump which incorporates means for automatically loading the flexible tubing into its operative position between the resiliently biased rollers and the backing.

Other objects, features and advantages of the invention will appear more clearly from the following detailed description of a preferred embodiment thereof made with reference to the accompanying drawings in which.

Figure 1:
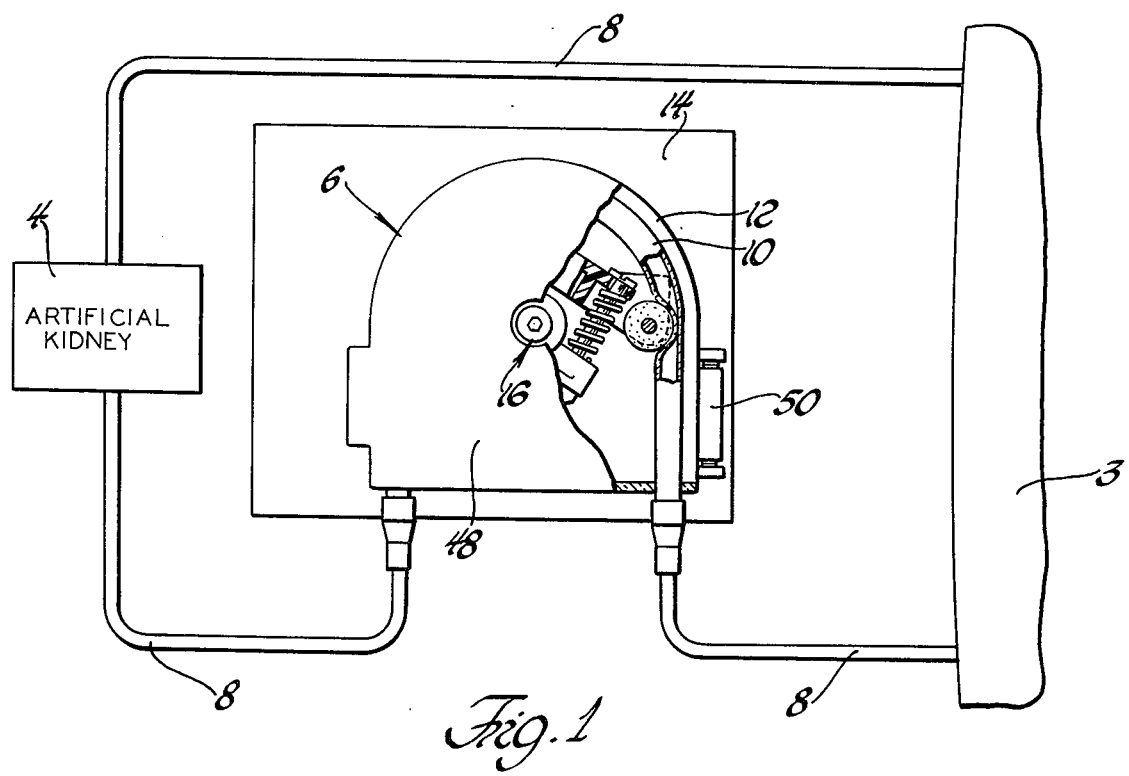
FIG. 1 is a view, partially schematic and partially with parts broken away, of an extracorporeal blood circulation system incorporating the present invention.

Referring now to FIG. 1, the reference numeral 3 depicts the body of the patient, 4 is an artificial kidney, 6 is the pump of the present invention, 8 represents the tubing which carries the patient's blood from the patient to and between the various components and then back to the patient, and 10 represents the flexible portion of the tubing which functions as a component of the pump 6. It will be understood that such extracorporeal blood circulation systems may contain additional components such, for example, as an air bubble detector, a heparin supply and pump, one or more drip chambers for removing air bubbles from the blood, and alarm devices actuated by abnormalities as, for example, in the blood pressure within the system.

Figure 2:
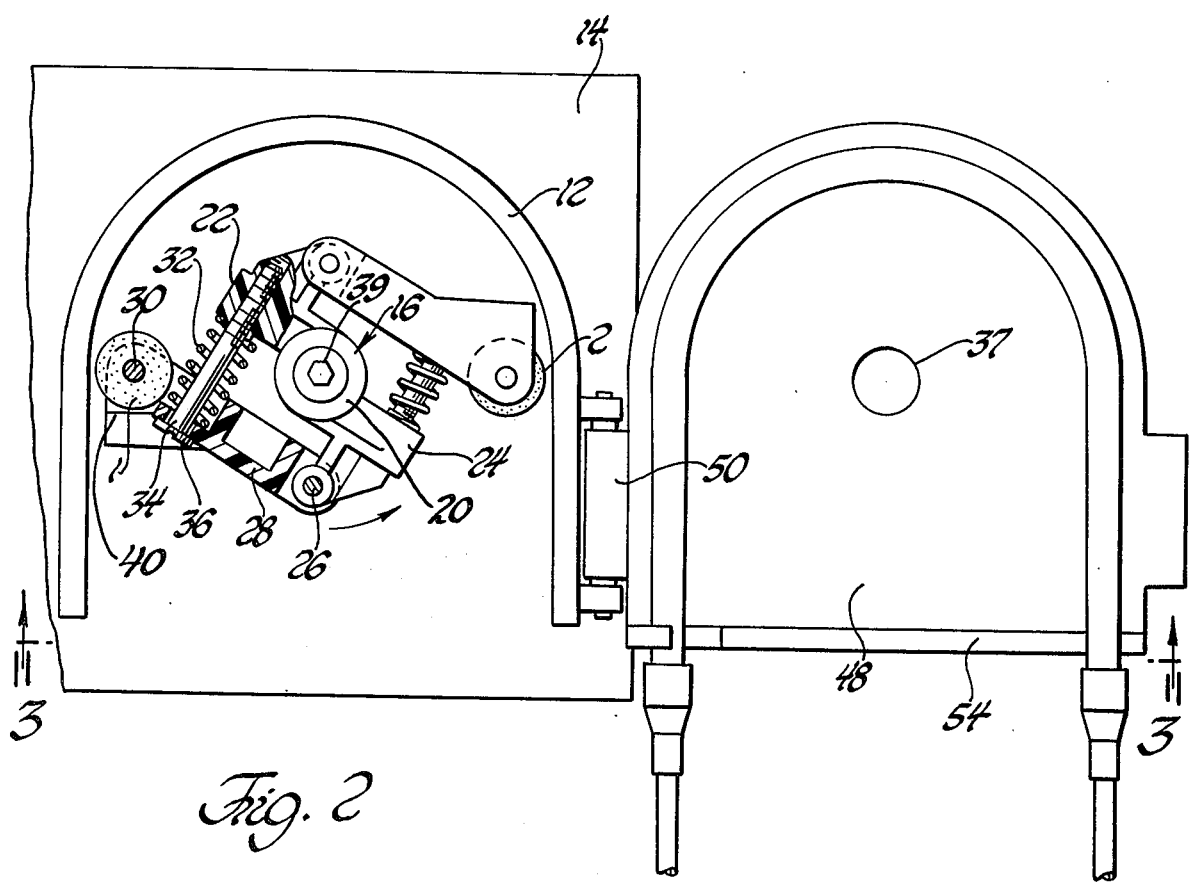
FIG. 2 is a front view of the pump embodied in the system shown in FIG. 1, the pump being shown in FIG. 2 in its open position, i.e. before the flexible tube has been loaded into its operative position therein.
Figure 3:
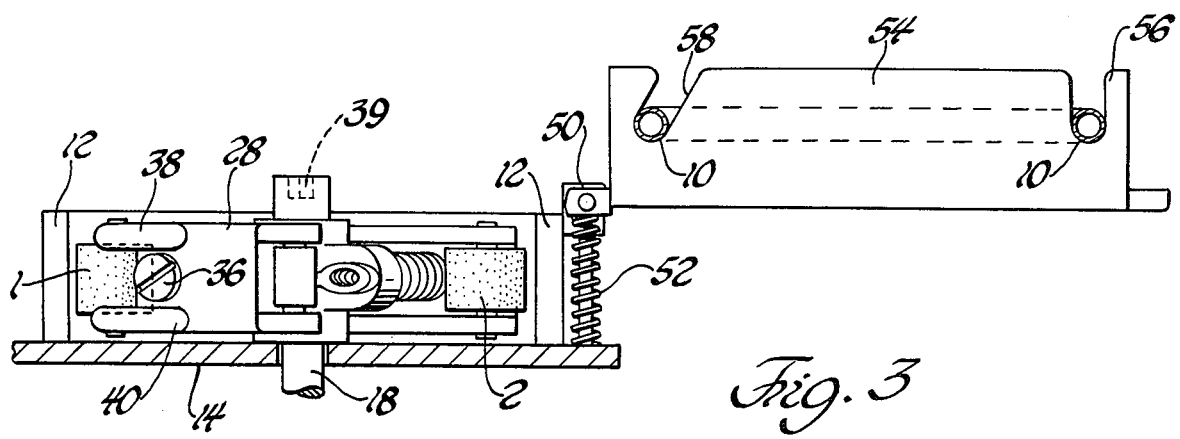
FIG. 3 is a view taken on the line 3—3 of FIG. 2.

Referring now to FIGS. 1–3, the preferred pump shown comprises an inverted U-shaped member 12, which functions as a tube backing member, secured to a flat panel 14. The upper arcuate portion of the member 12 is of uniform radius of curvature or, in other words, is of generally semicircular configuration. Within the member 12 is a rotor 16 driven by a concentric shaft 18 (see FIG. 3) which extends through the panel 14 and is there connected to a suitable drive means for the rotor, such as an electric motor, not shown. The rotor is concentric with the arcuate semicircular upper portion of the member 12.

The rotor includes a hub 20 having a pair of generally diametrically opposed outward extensions 22 and 24 each having a pivotally connected arm terminating in a roller resiliently biased radially outwardly toward the arcuate member 12. Since the structure of each of the extensions, and its associated assembly of components, is the same as that of the other, a description of one will serve as a description of both.

Pivotally connected by the shaft 26 to the extension 24 is an arm 28. The arm 28 is generally parallel to extension 22 and terminates with a roller 1 rotatably connected to the end of the arm by a shaft 30. The roller at the end of the arm pivotally connected to extension 22 is shown at 2.

Extending between the extension 22 and arm 28 is a coil spring 32 which resiliently biases arm 28 and its associated roller 1 generally radially outwardly from the hub toward the arcuate member 12. A spring guide pin 34 which has a head 36 abutting the outer surface of the arm 28 and which is threaded into extension 22 but slidably movable through an opening in arm 28 maintains the compressed coil spring 32 properly positioned and limits the radially outward extent to which the arm 28 and its associated roller 1 can proceed under the spring bias of the coil spring 32. A slot can be provided in the head of the threaded pin 34 to facilitate threading it in or out of extension 22 and thereby adjusting the extent of outer radial movement of the roller.

It will be seen that as the rotor is turned by its drive means in a counterclockwise direction the rollers 1 and 2, which are 180° apart, sequentially roll along the inner surface of the upper circular portion of the member 12 while being resiliently biased radially outwardly — the resilient bias being caused by the coil springs and being sufficient to occlude or squeeze the tube closed in the area of contact of the roller with the tube after the tube is inserted. After each of the rollers reaches the lower end of the arcuate portion of the U-shaped backing member it moves out of contact, but the head portion of its associated spring guide pin limits the radial outer movement of the roller as the head portion comes into abutting contact with its associated arm.

The hub of the rotor is provided with an extension which fits through an opening 37 in the door 48 (yet to be described) when the door is closed, the extension having a hexagonal opening 39 therein. (See FIGS. 2 and 3) This is simply a safety feature for use in the event of a power failure. That is, if the motor driving the rotor stops, the rotor can be manually operated by inserting the hexagonal end of a tool, such as a crank, into the opening 39 and then applying the rotory motion to the rotor by means of such tool.

In front of each roller (i.e. in front of the roller in the direction of rotation of the rotor), is a pair of outwardly extending tube guides, the guides for roller 1 being shown at 38 and 40, as can best be seen in FIGS. 3–6. The guides are spaced, one being positioned adjacent one axial end of the roller and the other being positioned adjacent the other axial end of the roller. In the embodiment shown these guides are integral with the arm for the roller (the arm being of molded organic resin), each guide consisting of a flat portion 42 (best seen in FIG. 5) terminating in a rounded portion 44 of somewhat greater thickness. Hence, as each of the rollers moves through its rotary movement as a part of the rotor, it is always immediately preceded, in the direction of rotation of the rotor, by the two spaced guides, one adjacent each axial end of the roller.

A door or cover 48, which functions as a tube positioning member for the backing member 12, is hinged to the member 12 along one of the straight leg portions thereof, the hinge being shown at 50. Associated with the hinger is a compressed coil spring 52 (see FIGS. 3–6) which is biased against the hinge, the hinge having flat sides and an arcuate end surface such that it functions as a cam. Hence when the door is in any of the positions shown in FIGS. 4–6 it is resiliently biased by the spring toward its closed position, i.e. toward its position against the member 12. However, when the door is in any position over-center of the arcuate end surface of the hinge in the direction toward the open position of the door, the spring biases the door toward its position as shown in FIG. 3, i.e. its open position.

Figure 6:
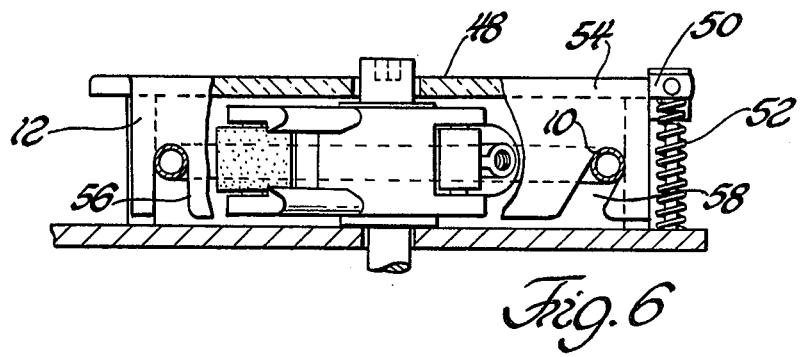
FIG. 6 is a view similar to that of FIG. 5, but with the tube fully loaded into its operative position in the pump.

The bottom of the door has an inwardly extending flange 54 (i.e. a flange extending toward panel 14 when the door is in its closed position) and in each side of this flange 54 is an elongated notch, such notches being shown at 56 and 58. (See FIG. 3) These notches function as brackets for removably receiving the flexible tube 10. The width of the notches is just very slightly less than the external diameter of the flexible tubing 10 being inserted into the pump, and the notches are oriented to position the tube portions inserted therein to be parallel to and adjacent the inner surfaces of the legs of the U-shaped member 12. In the preferred embodiment shown, notch 58 is at an angle such that when the door is closed, notch 58 extends, from the open end to the closed end of the notch, in a direction toward the inner surface of member 12. Notch 56, on the other hand, extends parallel to the inner surface of the member 12 when the door is closed. The closed rounded ends of each of the notches 56 and 58 are adjacent the middle of the inner surface of member 12, along its longitudinal axis, when the door is closed, as best seen in FIG. 6. The significance of these features will be discussed below in connection with the operation of the device.

Operation is as follows.

Figure 4:
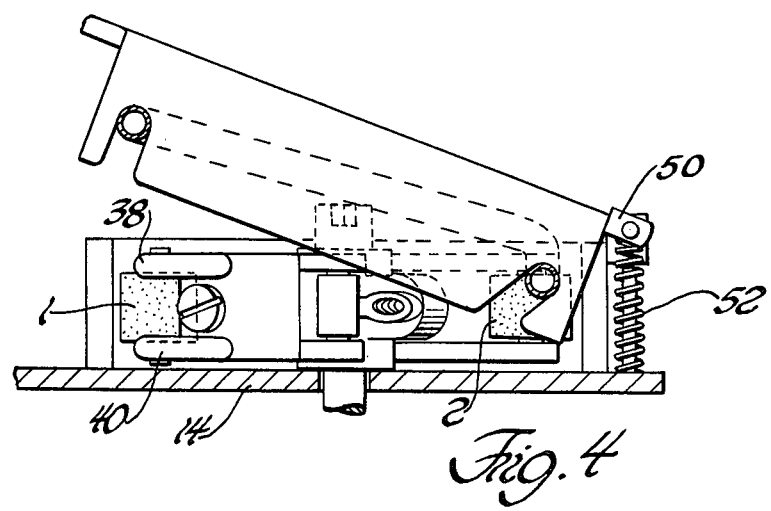
FIG. 4 is a view similar to that of FIG. 3 but just prior to the tube being commenced to be loaded into its operative position.

With the door 48 held in its open position by the resilient bias of the spring 52 (as shown in FIGS. 2 and 3) the flexible tubing 10 is snapped into the notches 56 and 58, and with a portion of the flexible tubing between the brackets forming a U-shape approximately equal to or slightly less than that of the inner surface of the U-shaped member 12. As indicated, that is shown in FIGS. 2 and 3. With this accomplished the door is moved toward its closed position and as soon as the door reaches a position over-center toward its closed position the spring 52 resiliently biases the door toward the closed position as shown in FIG. 4. The rotor is then actuated whereby the rotor commences its counter-clockwise movement. At the time the tube 10 is so installed and the rotor actuated, it makes no difference what the location of the rollers might be relative to the member 12 since in any case one of the rollers and its associated guides will, upon actuation of the rotor, automatically position the flexible tube 10 between the rollers and the inner surface of the member 12. But for purposes of description it will be assumed that the position of these rollers, at the time the tube 10 is inserted into the door flange notches and the door is allowed to close and the rotor actuated, is as shown in FIGS. 2 and 3 - and hence the description will be referenced to roller 1 and its associated guides though it could just as well be referenced to roller 1 and its associated guides if the circular orientation of the rollers were different than as shown at the time the door is closed and the rotor actuated.

Figure 5:
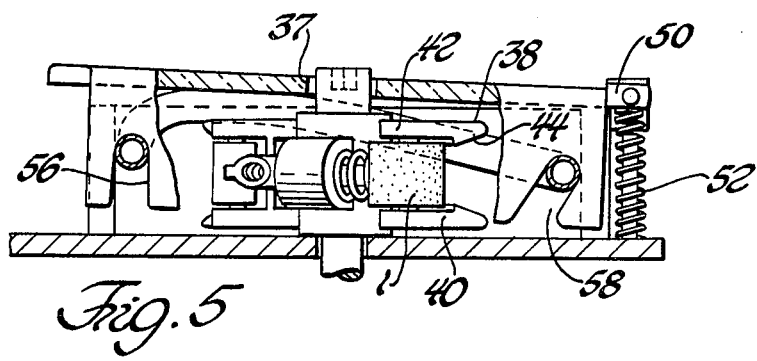
FIG. 5 is a view similar to that of FIG. 4 but with the tube partially loaded into its operative position.

When the pair of guides 38 and 40, immediately followed by roller 1, reach a position adjacent the hinged side of the cover, the inner surface of the thick outer portion 44 of guide 38 contacts the flexible tube portion positioned immediately above the notch 58 and, as the guides proceed in their rotary motion, the tube portion is biased and flexed by guide 38 laterally inwardly, i.e. toward the panel 14, and therefore into a position against or closely adjacent the inner surface of the member 12. This is shown in FIG. 5. Hence, the roller 1 immediately following such a pair of guides makes rolling contact with this tube portion. Because the rounded closed end of notch 58 is adjacent the middle of the member 12, along its longitudinal axis, the notch assists in maintaining the tube in this position so that the tube is contacted by the axial center portion of the roller 1 when the roller comes into contact with the tube. Also, the distance between the inner surfaces of guides 38 and 40 is such as to maintain the tube in such position, i.e. under the axial center portion of the rollers.

As the pair of guides 38 and 40 continue to move around and adjacent the inner circumference of the upper arcuate portion of the member 12, they continue to laterally displace the flexible tubing toward the panel and hence closely adjacent or against the inner surface of the member 12, all the while being followed by the associated roller 1 which progressively makes the rolling contact with the tube. Hence, by the time the pair of guides 38 and 40 reach the side of the cover opposite that of the hinge 50 the flexible tube is fully loaded into its operative position between the inner surface of the U-shaped member 12 and the resiliently biased rollers 1 and 2. At this point the resiliently biased cover completely closes against the U-shaped member and the loading operation is complete and the pump is in full operation. This is shown at FIG. 6.

After use of the device is completed (i.e. treatment of the patient by circulation of the blood through the artificial kidney is completed) and it is desired to unload the tube from the pump, it is only necessary to open the door 48 while the rotor is left in operation. When the door commences to be opened the slot 56, because it extends parallel to the inner surface 12 (and hence perpendicular to the plane of the U-shaped portion of the tubing in the pump), simply pulls away from the tubing leaving the tubing in the pump. However, prior to the door being fully opened (as in a position such as shown in FIG. 4) the slot 58 moves the tube portion immediately adjacent the notch 58 laterally away from the inner surface of member 12 and hence in a direction away from panel 14. After this occurs and a set of guides, for example guides 38 and 40, reach such portion of the tube, the outer surface of the outer guide, e.g. guide 38, contacts the tube and as the guides continue their rotary movement the tube is sequentially unloaded, the unloading being complete when the other roller reaches a position where it is out of contact with the tube. With the tube thus unloaded, the rotor can be turned off. It should be noted that even if notch 58 were oriented in the same direction as, i.e. parallel to, notch 56, the notch 58 would nevertheless move the flexible tube outwardly upon opening the door — this because of the short radius of the arcuate movement of the notch 58 when the door is opened. However, by orienting notch 58, as shown, there is greater or more rapid movement of the flexible tubing from the member 12 when the door is opened.

Hence, by way of the invention it is possible for the medical attendant or the patient to safely, conveniently and rapidly cause the automatic loading, and also unloading, of the flexible tubing into and from the roller pump, and with full assurance that the tubing will, when loaded, be positioned precisely as it should be — between the backing and the axial center portions of the spring biased rollers. That is, for loading, it is merely a matter of snapping the two spaced portions of the flexible tubing into the notches, with the upwardly extending U-shaped portion of the tubing therebetween, moving the door to its over-center position from where it is spring biased toward its closed position, and then actuating the rotor. As for unloading, it is simply a matter of opening the door prior to deactuating the rotor.

It will be understood that while the invention has been described specifically with reference to a preferred embodiment thereof, various changes and modifications may be made all within the full intended scope of the claims which follow. For example, instead of using springs to bias the rollers against the flexible tube, the outer portions of the rollers themselves can be of resilient material such as rubber or, alternatively, the inner surface of member 12 can be lined with resilient material such that there is a resilient bias of the tube against the rollers without the rollers themselves being spring biased. Likewise, the rotor construction, shape of the backing member 12 and door construction as shown, though preferred, are not essential to the practice of the invention in its broadest scope.

The embodiments of the invention in which an exclusive property or privelege is claimed are defined as follows:

1. An extracorporeal blood circulation system for circulating a patient's blood from and then back to the patient through tubing at least a portion of which is flexible, said system including a pump to cause the blood to circulate through the system, said pump comprising a backing member at least a portion of which is of arcuate shape receiving thereagainst said flexible portion of said tubing when said pump is operable, a rotor having rotatably secured thereto a plurality of rollers for contact with the flexible tubing portion to occlude said tubing portion in the areas of contact of each roller therewith thereby to pump blood through the tubing in the direction of rotation of the rotor, a tube positioning member for positioning said flexible tubing portion adjacent said backing member, and means connected to said rotor to move the flexible tubing portion from its position adjacent said backing member to a position between said rollers and said backing member upon actuation of said rotor, said tube positioning member comprising a member connected to said backing member and movable from a position away from said backing member to a position adjacent said backing member, and tube securing means on said tube positioning member for removably securing thereto said flexible tubing portion.

2. An extracorporeal blood circulation system as set forth in claim 1 wherein said means comprises an outwardly extending guide in front of each roller for contacting said tube portion in its position adjacent said backing member.

3. An extracorporeal blood circulation system as set forth in claim 1 wherein said tube securing means comprises a bracket on said tube positioning member oriented such that when the tube positioning member is moved from its position adjacent said backing member to its position away from said backing member said bracket moves the flexible tubing portion away from said backing member.

4. An extracorporeal blood circulation system as set forth in claim 1 wherein said tube positioning member is resiliently biased toward its position adjacent said backing member.

5. An extracorporeal blood circulation system as set forth in claim 4 wherein said tube positioning member is pivotally secured to said backing member.

6. An extracorporeal blood circulation system as set forth in claim 5 wherein said tube securing means comprises a bracket for snugly receiving said flexible tubing portion adjacent the pivotal connection between the backing member and the tube positioning member.

7. An extracorporeal blood circulation system as set forth in claim 6 wherein said bracket is oriented such that when the tube positioning member is pivoted away from said backing member said bracket moves the flexible tubing portion adjacent said bracket away from said backing member.

8. An extracorporeal blood circulation system for circulating a patient's blood from and then back to the patient through tubing at least a portion of which is flexible, said system including a pump to cause the blood to circulate through the system, said pump comprising a backing member having an arcuate portion receiving thereagainst said flexible portion of said tubing when said pump is operable, a rotor within said backing member having rotatably secured thereto a plurality of rollers for resiliently biased contact with the flexible tubing portion received against said arcuate portion of said backing member to occlude said tubing portion in the area of contact of each roller therewith thereby to pump blood through the tubing in the direction of rotation of the rotor, a tube-positioning member connected to said backing member and movable from a position away from said backing member to a position adjacent said backing member, tube-securing means on said tube positioning member for removably receiving said flexible tubing portion while said tube positioning member is in its position away from said backing member, and tube guide means connected to said rotor to move the flexible tubing portion secured to said tube positioning member to a position between said rollers and said backing member upon said tube positioning member being moved to its position adjacent said backing member and upon actuation of said rotor.

9. An extracorporeal blood circulation system as set forth in claim 8 wherein said tube securing means comprises a bracket which moves the flexible tube portion away from said backing member when said tube positioning member is moved from its position adjacent said backing member to its position away from said backing member.

10. An extracorporeal blood circulation system as set forth in claim 8 wherein said tube guide means comprises a pair of outwardly projecting guides in front of each roller, in the direction of rotation of said rotor, one of said projecting guides being adjacent one axial end of the roller and the other of said projecting guides being adjacent the other axial end of the roller.

11. An extracorporeal blood circulation system as set forth in claim 8 wherein there are two rollers spaced 180° apart.

12. An extracorporeal blood circulation system as set forth in claim 8 wherein said backing member has leg portions extending from said arcuate portion.

13. An extracorporeal blood circulation system as set forth in claim 12 wherein said tube positioning member is pivotally secured to one of the legs of said backing member.

14. An extracorporeal blood circulation system as set forth in claim 13 wherein said tube positioning member serves as a cover for said backing member and wherein the tube securing means comprises a pair of brackets on said cover adjacent the ends of the leg portions of the backing member.

* * * * *